United States Patent [19]

Pelrine

[11] 4,100,262
[45] Jul. 11, 1978

[54] SYNTHESIS OF ZEOLITE ZSM-5

[75] Inventor: Bruce Patrick Pelrine, Trenton, N.J.

[73] Assignee: Mobil Oil Corporation, New York, N.Y.

[21] Appl. No.: 824,379

[22] Filed: Aug. 15, 1977

[51] Int. Cl.$^2$ .......................... C01B 33/28; C07F 5/06
[52] U.S. Cl. ............................... 423/329; 252/431 N; 252/455 Z; 260/448 C; 423/328
[58] Field of Search ................................. 423/328–330; 260/448 C; 252/431 N, 455 Z

[56] References Cited

U.S. PATENT DOCUMENTS

| 3,702,886 | 11/1972 | Argauer et al. | 423/328 |
| 3,849,463 | 11/1974 | Dwyer et al. | 260/448 C |
| 3,947,482 | 3/1976 | Albers et al. | 260/448 C |
| 4,061,717 | 12/1977 | Kerr et al. | 423/329 |

*Primary Examiner*—Edward J. Meros
*Attorney, Agent, or Firm*—Charles A. Huggett; Raymond W. Barclay; Dennis P. Santini

[57] ABSTRACT

As synthesized by conventional technique, zeolite ZSM-5 crystals are cubic with some twinning and measure in size over the range of from about 3 × 3 microns to about 8 × 8 microns. By synthesizing crystalline aluminosilicate zeolite ZSM-5 according to the present method, i.e. in the presence of a tetraureacobalt (II) complex and with a specifically defined reaction mixture composition, the crystalline product will consist of highly twinned rectangular prismatic crystals exhibiting extreme uniformity in size of from about 5 × 10 microns to about 10 × 20 microns, depending on the ratio of said tetraureacobalt (II) complex to silica in the zeolite synthesis reaction mixture. Synthesis of ZSM-5 in accordance hereto will provide a zeolite with enhanced catalytic activity for certain chemical reactions.

10 Claims, No Drawings

SYNTHESIS OF ZEOLITE ZSM-5

BACKGROUND OF THE INVENTION

1. Field of the Invention

The present invention relates to a new method for synthesizing zeolite ZSM-5 and to use of the ZSM-5 synthesized hereby as catalyst for certain chemical conversion reactions. More particularly, it relates to making and using ZSM-5 which, in its as synthesized form, is comprised of highly twinned, rectangular prismatic crystals exhibiting extremely uniform size of between about 5 × 10 microns and about 10 × 20 microns.

2. Summary of the Prior Art

Zeolite ZSM-5 is a relatively new zeolite which in its conventionally synthesized aluminosilicate form has the following composition expressed in terms of mole ratios of oxides in the anhydrous state:

$$(0.9 \pm 0.2) M_{2/n}O : Al_2O_3 : xSiO_2$$

wherein M is selected from the group consisting of a mixture of tetraalkylammonium cation, the alkyl groups of which contain 2–5 carbon atoms, and alkali metal cations, especially sodium, and $x$ is at least 5, said cations having the valence $n$. ZSM-5 has a distinctive X-ray diffraction pattern which further identifies it from other known zeolites. The original alkali metal cations of ZSM-5 can be exchanged by ion exchange with other ions to form species of the zeolite which have exceptional catalytic properties. Zeolite ZSM-5 and its conventional preparation are the subject of U.S. Pat. No. 3,702,886, the disclosure of which is incorporated herein by reference.

SUMMARY OF THE INVENTION

In accordance with the present invention there is provided a method for preparing a new crystalline form of ZSM-5. The present invention also provides a method for using the new crystalline form of ZSM-5 in certain chemical conversion reactions.

DESCRIPTION OF SPECIFIC EMBODIMENTS

Zeolite ZSM-5 has been conventionally prepared by forming a mixture of alumina, silica, alkali metal oxide, water and tetraalkylammonium compounds such that the mixture has a composition, in terms of mole ratios of oxides, falling within the following range:

| | | |
|---|---|---|
| $SiO_2/Al_2O_3$ | = | 5–100 |
| $H_2O/SiO_2$ | = | 0.7–3000 |
| $OH^-/SiO_2$ | = | 0.07–10.0 |
| $M/SiO_2$ | = | 0.3–3.0 |
| $R/SiO_2$ | = | 0.01–2.0 | wherein M is an alkali metal ion, such as sodium, and R is a tetraalkylammonium cation, the alkyl groups of which contain 2–5 carbon atoms. The reaction mixture is maintained at a temperature of from about 100° F to about 400° F until crystals of ZSM-5 are formed.

Zeolite ZSM-5 possesses a definite distinguishing crystalline structure whose X-ray diffraction pattern shows the following significant lines:

TABLE I

| Interplanar Spacing d (Å) | Relative Intensity |
|---|---|
| 11.1 ± 0.3 | S |
| 10.0 ± 0.3 | S |
| 7.4 ± 0.2 | W |
| 7.1 ± 0.2 | W |
| 6.3 ± 0.2 | W |
| 6.04 ± 0.2 | W |
| 5.56 ± 0.1 | W |
| 5.01 ± 0.1 | W |
| 4.60 ± 0.08 | W |
| 4.25 ± 0.08 | W |
| 3.85 ± 0.07 | VS |
| 3.71 ± 0.05 | S |
| 3.04 ± 0.03 | W |
| 2.99 ± 0.02 | W |
| 2.94 ± 0.02 | W |

These values were determined by standard technique. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in Å, corresponding to the recorded lines, were calculated. In Table I the relative intensities are given in terms of the symbols W = weak, S = strong and VS = very strong. It should be understood that this X-ray diffraction pattern is characteristic of all the species of ZSM-5 zeolites. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

In the present method of preparing a ZSM-5 crystalline aluminosilicate zeolite, a reaction mixture is prepared comprising sources of alkali metal, alumina, silica, one or more tetraalkylammonium compounds, water and a tetraureacobalt (II) complex. The reaction mixture has the following composition expressed in terms of mole ratios of oxides:

| | | |
|---|---|---|
| $SiO_2/Al_2O_3$ | = | 5–100 |
| $H_2O/SiO_2$ | = | 0.7–3000 |
| $OH^-/SiO_2$ | = | 0.07–10.0 |
| $X/SiO_2$ | = | 0.0047–0.047 |
| $M/SiO_2$ | = | 0.3–3.0 |
| $R/SiO_2$ | = | 0.01–2.0 | wherein M and R are as above defined and X is a tetraureacobalt (II) complex, such as, for example, tetraureacobalt (II) nitrate. The reaction mixture is maintained at a temperature of from about 100° F to about 400° F for a period of time of from about 3 hours to about 180 days until crystals of ZSM-5 are formed. The solid product is separated from the reaction medium, as by cooling the whole to room temperature, filtering and water washing. A more preferred temperature range is from about 180° F to about 350° F for a period of time at a temperature within such preferred range being from about 3 hours to about 30 days.

In addition to providing a uniformly sized form of ZSM-5 which can be used as a catalyst, it is interesting to note that the present method of preparation of ZSM-5 also provides the benefit of producing a product zeolite having a somewhat higher $SiO_2/Al_2O_3$ ratio than a zeolite prepared by the conventional method.

The composition for the synthesis of synthetic ZSM-5 can be prepared utilizing materials which can supply the appropriate oxide. Such materials include aluminates, alumina, silicates, silica hydrosol, silica gel, silicic acid and hydroxides. It will be understood that each oxide component utilized in the reaction mixture for preparing ZSM-5 can be supplied by one or more essential reactants and they can be mixed together in any order. For example, any oxide can be supplied by an aqueous solution, sodium hydroxide or by an aqueous solution of a suitable silicate; the cation can be supplied by a compound of that cation, such as, for example, a salt. The tetraureacobalt (II) complex can be supplied by an appropriate compound such as the nitrate, nitrite, sulfate, hydroxide, halide or the like, thereof. Crystallization time of the new crystal form ZSM-5 will vary with the nature of the reaction mixture employed.

The ZSM-5 composition as prepared hereby has the characteristic X-ray diffraction pattern of conventionally prepared ZSM-5, the values of which are set forth in Table I.

The presently prepared new crystal form ZSM-5 can be utilized as catalytic material for a number of hydrocarbon conversion reactions substantially as synthesized or the original cations of the as synthesized ZSM-5 can be replaced in accordance with techniques well known in the art, at least in part, by ion exchange with other cations. When used as synthesized, the zeolite is preferably heated to a temperature within the range of from 150° F to about 1500° F for a period of time ranging from about 1 hour to about 48 hours or more. Preferred replacing cations include metal ions, ammonium ions, hydrogen ions and mixtures thereof. Particularly preferred cations are those which render the zeolite catalytically active especially for hydrocarbon conversion. These include hydrogen, rare earth metals, aluminum, metals of Groups IIA, IIIB, IVB, VIB, VIII, IB, IIB, IIIA, IVA. Of the replacing metallic cations, particular preference is given to cations of metals such as rare earth, Mn, Ca, Mg, Zn, Cd, Pd, Ni, Cu, Ti, Al, Sn, Fe and Co.

A typical ion exchange technique would be to contact the synthetic ZSM-5 zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the zeolite is then preferably washed with water and dried at a temperature ranging from 150° F to about 600° F and thereafter may be calcined in air or other inert gas at temperatures ranging from about 500° F to 1500° F for periods of time ranging from 1 to 48 hours or more to produce a catalytically-active thermal decomposition product thereof.

Regardless of the cation replacing the cations in the synthesized from of the ZSM-5, the spatial arrangement of the aluminum, silicon and oxygen atoms which form the basic crystal lattices of the new crystal form ZSM-5 remains essentially unchanged by the described replacement of the original cations as determined by taking an X-ray powder diffraction pattern of the ion-exchanged material.

The hereby prepared zeolite ZSM-5 may be used in a wide variety of organic compound, e.g. hydrocarbon compounds and oxygenates such as methanol, conversion processes. Particular enhancement in catalytic activity for certain chemical reactions when compared to conventionally synthesized ZSM-5 may be observed.

Catalytic processes in which ZSM-5 may be used include, for example, alkylation of aromatics with olefins, aromatization of normally gaseous olefins and paraffins, aromatization of normally liquid low molecular weight paraffins and olefins, isomerization of aromatics, paraffins and olefins, disproportionation of aromatics, transalkylation of aromatics, oligomerization of olefins and cracking and hydrocracking. The new crystal form ZSM-5 exhibits enhanced catalytic activity in the processes of converting methanol to ethylene and gasoline and production of p-xylene via toluene disproportionation. All of the foregoing catalytic processes are of value since they result in upgrading of the organic charge being processed.

Synthetic ZSM-5 zeolites prepared in accordance hereto can be used either in the organic cation or alkali metal form and hydrogen form or another univalent of multivalent cationic form. They can also be used in intimate combination with a hydrogenating component such as tungsten, vanadium, molybdenum, rhenium, nickel, cabalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to ZSM-5 such as, for example, by, in the case of platinum, treating the zeolite with a platinum metal-containing ion. Thus, suitable platinum compounds for this purpose include chloroplatinic acid, platinous chloride and various compounds containing the platinum amine complex. Combinations of metals and methods for their introduction can also be used.

ZSM-5 prepared by the instant invention, being composed of very uniformly sized crystals, may be formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially and then extruded.

In the case of many catalysts, it is desired to incorporate the ZSM-5 hereby prepared with another material resistant to the temperatures and other conditions employed in organic conversion processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the ZSM-5, i.e. combined therewith, which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the hereby synthesized ZSM-5 catalyst include the montmorillonite and kaolin family, which families include the sub-bentonites, and the kaolins commonly known as Dixie, McNammee, Georgia and Florida clays or others in which the main mineral constituent is halloysite, kaolinite, dickite, nacrite, or anauxite. Such clays can be used in the raw state or initially subjected to calcination, acid treatment or chemical modification.

In addition to the foregoing materials, the ZSM-5 catalyst hereby synthesized can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mxiture of these components could also be used. The relative proportions of finely divided crystalline aluminosilicate ZSM-5 and inorganic oxide gel matrix vary widely with the crystalline aluminosilicate content ranging from about 1 to about 90 percent by weight and more usually in the range of about 2 to about 50 percent by weight of the composite.

For conversion of organic compounds in general, the organic compound or feedstock containing same may be contacted with a catalyst containing the hereby prepared zeolite ZSM-5, at a temperature between about 100° F and about 1400° F, a pressure between about atmospheric and about 200 atmospheres, a hydrogen/organic compound mole ratio of between 0 and about 80, and a weight hourly space velocity (WHSV) of from about 0.1 $hr^{-1}$ to about 1000 $hr^{-1}$.

More specifically, when said conversion involves polymerization of olefin-containing liquid or gaseous feedstocks the temperature will be between about 500° F and about 900° F, the pressure will be from about atmospheric to about 50 atmospheres and the WHSV will be from about 0.5 $hr^{-1}$ to about 50 $hr^{-1}$. When said conversion is aromatization of gaseous or liquid feedstocks which may be olefinic or paraffinic with or without aromatics present, the temperature will be from about 800° F to about 1200° F, the pressure will be from about atmospheric to about 10 atmospheres and the WHSV will be from about 0.1 $hr^{-1}$ to about 10 $hr^{-1}$. When said conversion is the alkylation of aromatics, such as benzene or toluene, with an alkylating agent of an olefin or alcohol, reaction conditions will include a temperature of from about 400° F to about 1000° F, a pressure of from about atmospheric to about 60 atmospheres, a WHSV of from about 0.5 $hr^{-1}$ to about 50 $hr^{-1}$ and an aromatic compound/alkylating agent mole ratio of from about 2 to about 200. When said conversion is isomerization of aromatics such as xylenes, reaction conditions will include a temperature of from about 300° F to about 900° F, a pressure of from atmospheric to about 60 atmospheres, and a WHSV of from about 0.2 $hr^{-1}$ to about 100 $hr^{-1}$. When said conversion is isomerization of paraffins or olefins, reaction conditions will include a temperature of from about 100° F to about 700° F, a pressure of from atmospheric to about 60 atmospheres, and a WHSV of from about 0.1 $hr^{-1}$. When said conversion is disproportionation of aromatics, such as toluene, reaction conditions will include a temperature of from about 600° F to about 1150° F, a pressure of from atmospheric to about 50 atmospheres, and a WHSV of from about 0.5 $hr^{-1}$ to about 20 $hr^{-1}$. When said conversion is transalkylation of aromatics, such as benzene, with alkylaromatics, such as trimethylbenzenes, reaction conditions will include a temperature of from about 500° F to about 1100° F, a pressure of from atmospheric to about 50 atmospheres, and a WHSV of from about 0.5 $hr^{-1}$ to about 20 $hr^{-1}$. When said conversion is oligomerization of olefins, such as propylene, reaction conditions will include a temperature of from about 500° F to about 1100° F, a pressure of from atmospheric to about 50 atmospheres, and a WHSV of from about 0.1 $hr^{-1}$ to about 1000 $hr^{-1}$. When said conversion is cracking of a gas oil or a residual oil, reaction conditions will include a temperature of from about 600° F to about 1400° F, a pressure of from atmospheric to about 10 atmospheres, and a WHSV of from about 0.5 $hr^{-1}$ to about 50 $hr^{-1}$. When said conversion is hydrocracking of hydrocarbon-containing feedstocks, such as resids or heavy petroleum stocks, reaction conditions will include a temperature of from about 400° F to about 850° F, a pressure of from about 10 atmospheres to about 200 atmospheres, a WHSV of from about 0.1 $hr^{-1}$ to about 10 $hr^{-1}$ and a $H_2$/hydrocarbon mole ratio of from about 2 to about 80.

In order to more fully illustrate the nature of the invention and the manner of practicing same, the following examples are presented.

EXAMPLE 1

A first solution was prepared to contain 0.57 grams of tetraureacobalt (II) nitrate, 2.10 grams of $Al_2(SO_4)_3 \cdot 18-H_2O$, 7.20 grams of sulfuric acid, 7.90 grams of tetrapropylamine bromide and 108 ml of water. A second solution was prepared to contain 63.3 grams of sodium silicate (28.5 wt. % $SiO_2$, 8.8 wt. % $Na_2O$ and 62.7 wt. % $H_2O$) and 80 ml of water.

A gel was formed upon addition of the first solution to the second solution, said gel exhibiting a tetraureacobalt (II) complex to $SiO_2$ mole ratio of about 0.0047. The gel was then placed in a steam bath at 208° F for 7 weeks. The resulting product having a crystallinity of about 45% was determined to comprise zeolite ZSM-5. The crystals of ZSM-5 uniformly measured 5 × 10 microns and the $SiO_2/Al_2O_3$ ratio thereof was 160.

The product of this example was slurried in 20% sodium hydroxide solution at 130° F for about 18 hours to remove essentially all amorphous material, thereby yielding 100% crystallic zeolite ZSM-5.

EXAMPLE 2

The procedure of Example 1 was again followed except for the fact that the amount of tetraureacobalt (II) complex in the first solution was 5.70 grams, thereby giving a tetraureacobalt (II) complex to $SiO_2$ mole ratio in the gel of about 0.047. The resulting product was about 45% crystalline zeolite ZSM-5 with crystals measuring uniformly 10 × 20 microns. The $SiO/Al_2O_3$ ratio of the ZSM-5 product of this example was determined to be 184.

The product of this example was slurried in 20% sodium hydroxide solution at 130° F for about 18 hours to remove essentially all amorphous material, thereby yielding 100% crystalline zeolite ZSM-5.

EXAMPLE 3

A quantity of the zeolite ZSM-5 prepared in Example 2 was contacted with solutions of ammonium chloride and cobalt nitrate, washed with water and then heated so that a portion of the sodium ions in the zeolite structure were exchanged for hydrogen and cobalt ions. The resulting CoH ZSM-5 zeolite of extremely uniform crystal size measuring 10 × 20 microns was contacted with methanol at a liquid hourly space velocity of 2, atmospheric pressure and a temperature of 590° F. At 43.7 weight percent conversion, the yield of ethylene was 24.3 weight percent of total product.

For comparison purposes, a zeolite ZSM-5, prepared in accordance with the conventional method and having sodium ions thereof exchanged with hydrogen and cobalt ions as above, produced a product containing only about 18 weight percent ethylene under the same reaction conditions and at the same methanol conversion as Example 3.

EXAMPLE 4

Another quantity of the zeolite ZSM-5 prepared in Example 2, having been ion-exchanged by contact with an ammonium chloride solution followed by water washing and heating, is contacted with a toluene feedstock and hydrogen under disproportionation conditions including a temperature of 1100° F, a pressure of one atmosphere, a hydrogen/toluene mole ratio of 2 and a WHSV of 10 hr$^{-1}$. At a toluene conversion of 20.7 weight percent, the ratio of p-xylene/total xylnes in the product is about 45.

For comparison purposes, a zeolite ZSM-5, prepared in accordance with the conventional method and having sodium ions thereof exchanged with hydrogen ions as above, gives a product exhibiting the p-xylene/total xyxlenes ratio at 20.7 weight percent conversion and the same reaction conditions as in Example 4 of about 37.

EXAMPLE 5

A fixed bed of HZSM-5 prepared as in Example 4 composed of crystals uniformly 10 × 20 microns in size in a reactor maintained at 700° F and atmospheric pressure is contacted with methanol at a WHSV of 2 hr$^{-1}$ to manufacture gasoline product. Analysis of gasoline product from the reactor indicates low durene make, averaging less than 2 weight percent of the hydrocarbon product. The $C_5+$ gasoline product contains about 40 percent aromatics and the fraction collected from the sixth to eighth day on stream has an octane number of about 95.5.

For comparison, two zeolite ZSM-5 samples, one composed of crystals about 0.02 micron in size and the other composed of crystals between 2 and 5 microns in size, and both hydrogen exchanged as in Example 4, provided a gasoline product under the same reaction conditions as in Example 5 containing durene in the hydrocarbon product of about 5.9 weight percent and 2.6 weight percent, respectively.

What is claimed is:

1. A method for synthesizing crystalline aluminosilicate zeolite ZSM-5 in a highly twinned, rectangular prismatic crystal form of uniform size which comprises the steps of preparing a reaction mixture containing sources of sodium oxide, tetraalkylammonium oxide, an oxide of aluminum, an oxide of silicon, water and a tetraureacobalt (II) complex and having a composition, in terms of mole ratios of oxides, falling within the following ranges:

| | | |
|---|---|---|
| $SiO_2/Al_2O_3$ | = | 5–100 |
| $H_2O/SiO_2$ | = | 0.7–3000 |
| $OH^-/SiO_2$ | = | 0.07–10.0 |
| $X/SiO_2$ | = | 0.0047–0.047 |
| $M/SiO_2$ | = | 0.3–3.0 |
| $R/SiO_2$ | = | 0.01–2.0 | wherein M is an alkali metal ion and R is a tetraalkylammonium cation, the alkyl groups of which contain 2–5 carbon atoms and X is a tetraureacobalt (II) complex, and maintaining said mixture at a temperature of from about 100° F to about 400° F until crystals of said zeolite are formed.

2. The method of claim 1 wherein the temperature is maintained between about 180° F and about 350° F.

3. The method of claim 1 which comprises the further step of replacing, at least in part, the original cations of said zeolite by ion exchange with a cation or a mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

4. The method of claim 2 which comprises the further step of replacing, at least in part, the original cations of said zeolite by ion exchange with a cation or a mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

5. The method of claim 1 which comprises the further step of heating said zeolite to a temperature in the range of 150° F to 1500° F.

6. The method of claim 2 which comprises the further step of heating said zeolite to a temperature in the range of 150° F to 1500° F.

7. The method of claim 3 which comprises the further step of heating said zeolite to a temperature of from 150° F to about 600° F.

8. The method of claim 4 which comprises the further step of heating said zeolite to a temperature of from 150° F to about 600° F.

9. The method of claim 7 which comprises the further step of calcining said zeolite to a temperature of from 500° F to 1500° F.

10. The method of claim 8 which comprises the further step of calcining said zeolite to a temperature of from 500° F to 1500° F.

* * * * *

UNITED STATES PATENT AND TRADEMARK OFFICE
CERTIFICATE OF CORRECTION

PATENT NO. : 4,100,262
DATED : July 11, 1978
INVENTOR(S) : BRUCE PATRICK PELRINE It is certified that error appears in the above-identified patent and that said Letters Patent are hereby corrected as shown below:

Column 4, line 20: "of" should be -- or --.

Column 4, line 24: "cabalt" should be -- cobalt --.

Column 5, line 62: "100 hr -1" should be -- 100 $hr^{-1}$ --.

Column 5, line 66: -- to about 2 $hr^{-1}$ -- should be inserted after "0.1 $hr^{-1}$".

Signed and Sealed this

Fifteenth Day of May 1979

[SEAL]

Attest:

RUTH C. MASON
Attesting Officer

DONALD W. BANNER
Commissioner of Patents and Trademarks